United States Patent
Kelchlin (10) Patent No.: US 9,498,311 B2
(45) Date of Patent: Nov. 22, 2016

(54) MULTIPURPOSE FILAMENT DISPENSING DEVICE

(71) Applicant: Christopher Edwin Kelchlin, Buffalo, NY (US)

(72) Inventor: Christopher Edwin Kelchlin, Buffalo, NY (US)

(*) Notice: Subject to any disclaimer, the term of this patent is extended or adjusted under 35 U.S.C. 154(b) by 0 days.

(21) Appl. No.: 14/636,858

(22) Filed: Mar. 3, 2015

(65) Prior Publication Data

US 2015/0245893 A1    Sep. 3, 2015

Related U.S. Application Data (60) Provisional application No. 61/947,083, filed on Mar. 3, 2014.

(51) Int. Cl.
| | |
|---|---|
| *A61C 15/00* | (2006.01) |
| *A61C 15/04* | (2006.01) |
| *A45D 40/18* | (2006.01) |
| *B65D 43/22* | (2006.01) |

(52) U.S. Cl.
CPC ............. *A61C 15/043* (2013.01); *A45D 40/18* (2013.01); *A61C 15/046* (2013.01); *B65D 43/22* (2013.01)

(58) Field of Classification Search
CPC .... A61C 15/00; A61C 15/04; A61C 15/043; A61C 15/046; A45D 44/18; A46B 15/0071; A46B 15/0073
See application file for complete search history.

(56) References Cited

U.S. PATENT DOCUMENTS

| | | | | |
|---|---|---|---|---|
| 1,733,114 A | * | 10/1929 | Brennan | A61C 15/043 132/314 |
| 2,233,522 A | * | 3/1941 | Fickle | A46B 11/001 132/309 |
| 3,890,986 A | * | 6/1975 | Gerlich | A46B 15/0071 132/309 |
| 4,852,770 A | * | 8/1989 | Sledge | B65D 47/0814 215/216 |
| 4,887,621 A | * | 12/1989 | Vallieres | A46B 5/0095 132/309 |
| 4,934,389 A | * | 6/1990 | Pettiford | A61C 15/043 132/324 |
| 5,076,302 A | * | 12/1991 | Chari | A61C 15/043 132/324 |
| 5,544,754 A | | 8/1996 | Stahl | |
| 5,607,050 A | * | 3/1997 | Dolan | A61C 15/043 132/325 |
| 5,732,722 A | * | 3/1998 | Mortvedt | A61C 15/043 132/325 |
| 5,979,706 A | * | 11/1999 | Grussmark | A61C 15/043 222/105 |
| 7,243,663 B1 | * | 7/2007 | Einstein, Jr. | A61C 15/043 132/314 |
| 8,381,743 B1 | * | 2/2013 | Thomas | A61C 15/043 132/325 |
| 8,511,323 B2 | | 8/2013 | Jimenez et al. | |
| 2005/0211263 A1 | * | 9/2005 | Kuo | A45D 44/18 132/310 |
| 2006/0196909 A1 | * | 9/2006 | Hadtke | A61C 15/043 225/39 |
| 2012/0257919 A1 | | 10/2012 | Silvers | |
| 2013/0252206 A1 | | 9/2013 | Lee | |

FOREIGN PATENT DOCUMENTS

KR    20110132830 A  * 12/2011

* cited by examiner

*Primary Examiner* — Robyn Doan
(74) *Attorney, Agent, or Firm* — Vincent G. LoTempio; Kloss, Stenger & LoTempio; David T. Stephenson (57) ABSTRACT

A multipurpose filament dispensing device serves the dual purpose of dispensing a filament, such as dental floss, while simultaneously forming a cap on a container of a topical composition. The device can either function as a standalone dispenser for storing and dispensing the filament, or serve as a cap for the container while simultaneously storing and dispensing the filament. The filament is rotatably extracted from an internal spool. The device dispenses a desired amount of filament from the spool, extending the filament from a raised outlet to a depressed cutting member. The downward slope of the filament facilitates grasping and manipulating of the filament. After extracting a desired unit length of the filament, the filament may be cut at a unit length with a sharp edge on the cutting member. The device forms a detachable cap over a container of topical composition, such as lip balm.

17 Claims, 7 Drawing Sheets

MULTIPURPOSE FILAMENT DISPENSING DEVICE

FIELD OF THE DISCLOSURE

The present disclosure relates generally to a multipurpose filament dispensing device. More so, a multipurpose filament dispensing device dispenses a filament from a raised outlet and extends the filament to a depressed cutting member to enable facilitated grasping and cutting of the filament, while simultaneously capping an opening on a container of a topical composition.

BACKGROUND OF THE DISCLOSURE

The following background information may present examples of specific aspects of the prior art (e.g., without limitation, approaches, facts, or common wisdom) that, while expected to be helpful to further educate the reader as to additional aspects of the prior art, is not to be construed as limiting the present disclosure, or any embodiments thereof, to anything stated or implied therein or inferred thereupon.

Typically, oral hygiene is a significant concern to many individuals. It is common practice for many to brush their teeth twice a day, once in the morning and once in the evening. Another important oral hygiene step is dental flossing. While teeth brushing may remove plaque formed on the surface of the teeth, dental floss assists in removing plaque that may form in between adjacent teeth.

It is known that dental floss is a cord of thin filaments used to remove food and dental plaque from between teeth. The floss is gently inserted between the teeth and wiped along the teeth sides, especially close to the gums or underneath them. Toothbrushes do not clean between teeth or below the gum line. Used as an addition to tooth brushing as part of regular oral hygiene flossing can reduce gingivitis and halitosis compared to tooth brushing alone. In dentistry, floss is classed as an interdental cleaning aid.

In many instances, lip balm is a wax-like substance applied topically to the lips of the mouth to moisturize and relieve chapped or dry lips, angular cheilitis, stomatitis, or cold sores. The primary purpose of lip balm is to provide an occlusive layer on the lip surface to seal moisture in lips and protect them from external exposure. Dry air, cold temperatures, and wind all have a drying effect on skin by drawing moisture away from the body.

Often, the hygiene for the mouth is performed at the same time to save time and effort. Thus, brushing teeth, flossing, applying lip balm, and chewing breath mints and gum. These different forms of hygiene generally utilize variously sized containers and applicators. Maintaining the myriad containers, applicators, and capping members in one place, and also organizing everything to be sufficiently compact for portability can be problematic.

Other proposals have involved combining a dental floss cap with a toothpaste cap. The problem with these devices is that they are limited to capping toothpaste, and access to the dental floss can be difficult, as the dental floss dispenses generally parallel to the top surface of the cap. Thus, an unaddressed need exists in the industry to address the aforementioned deficiencies and inadequacies. Even though the above cited methods for a dental floss dispenser and capping member meets some of the needs of the market, a multipurpose filament dispensing device that dispenses a filament from a raised outlet, and extends the filament to a depressed cutting member to enable facilitated grasping and cutting of the filament, while capping a container of topical ointment is still desired.

SUMMARY OF THE DISCLOSURE

The present disclosure is directed to a multipurpose filament dispensing device that dispenses a filament from a raised outlet, and extends the filament to a depressed cutting member to enable facilitated grasping and cutting of the filament. The device also caps an opening on a container of a topical composition. The device comprises an outer housing that substantially encases an inner housing. Both housings are arranged to work together to efficiently dispense the filament and cap the opening in the container.

The outer housing engages the opening in the container and forms a protective casing for the inner housing. The outer housing is defined by a cavity, an outlet end, a mounting end, and a lid. In one embodiment, the outer housing is generally circular and has a diameter substantially the same as the container that is being capped. The lid is configured to regulate access to the cavity. In one embodiment, a hinge forms a junction between the lid and the dispensing end to enable pivotal movement of the lid between an open position and a closed position.

The mounting end is oppositely positioned from the dispensing end and configured to enable engagement with an opening of a container. The mounting end can mate with the opening on the container through various mechanism, including, without limitation, threaded engagement, frictional fit, interlocking ridges, magnets, and screws. In this manner, the outer housing forms a cap to the opening of the container.

The inner housing encases a spool that carries the filament and facilitates grasping, manipulating, and cutting of the filament. The inner housing is defined by a dispensing end, a cap end, and an interior chamber. The inner housing is disposed to position inside the cavity of the outer housing, wherein the dispensing end and the outlet end are in a spaced-apart parallel arrangement. In one embodiment, the inner housing snaps/locks inside the cavity of the outer housing.

The dispensing end of the inner housing comprises a raised outlet, a depression, and a protrusion. The raised outlet is in communication with the interior chamber of the inner housing. In one embodiment, the raised outlet may include a generally circular opening that enables passage of the filament from the interior chamber. The depression and the protrusion enable secure positioning of components for accessing, manipulating, and cutting the filament, as described below.

The device may further include a spool post. The spool post is disposed in the interior chamber of the inner housing. The spool post extends along the length of the inner housing and rotatably mounts the post inside the inner housing. The spool is configured to carry a filament. The filament winds around the spool for storage, and may be unwound to dispense the filament from the elevated outlet. The filament may include, without limitation, dental floss.

The device may further include a panel that is used for cutting the filament. The panel is disposed to engage the depression of the dispensing end. Specifically, the panel is substantially shaped to rest flush inside the depression. The panel is defined by a panel opening and a cutting member. The panel opening is configured to interlock with the protrusion of the dispensing end. In one embodiment, the panel opening enables passage of the protrusion and a heat staking process is used to interlock the panel opening and the depression. However, in other embodiments, the panel opening may interlock with the protrusion through a frictional fit, a ridged mating, a magnetic lock, or an adhesive. In any case, the panel positions securely inside the depression of the dispensing end.

As discussed above, the cutting member has a generally sharp edge. The sharp edge of the cutting member is configured to enable separation of a unit length of dispensed filament from a section of filament wound on the spool. The sharp edge may form a semi-circular shape, though the radius may be increased or decreased to affect the cutting capacity. The cutting member extends from the panel at a slope. The slope creates a gap that facilitates passing the filament over the sharp edge.

Additionally, since the panel, and thereby the cutting member, are disposed in the depression, the raised outlet is generally at a higher elevation. Thus, as the filament dispenses from the raised outlet, the filament extends at a downward angle towards the cutting member. This sloped extension of filament from the raised outlet to the cutting member forms a space beneath the filament that facilitates manipulation and grasping of the filament. In essence, the difference in elevation between the raised outlet and the cutting member is configured to enable facilitated cutting of the filament.

One objective of the present disclosure is to a provide multipurpose filament dispensing device that dispenses dental floss and caps an opening in an existing container of a topical composition, such as lip balm or can be as a stand-alone device.

Another objective is to provide a multipurpose filament dispensing device that is configured to extend the filament at a downward angle from the raised outlet so as to form a space between the filament and the dispensing end of the inner housing, so that the filament is more easily grasped and manipulated for dispensing and cutting.

Another objective is to provide a multipurpose filament dispensing device having a cap end on the inner housing that restricts passage of the topical ointment that extrudes form the opening in the container.

Yet another objective is to provide a multipurpose filament dispensing device that utilizes heat staking to fasten a panel to a depression in a dispensing end.

Yet another objective is to provide an inexpensive way to manufacture and easy to use multipurpose filament dispensing device and cap for an opening of a pre-existing container.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The disclosure will now be described, by way of example, with reference to the accompanying drawings, in which.

Like reference numerals refer to like parts throughout the various views of the drawings.

DETAILED DESCRIPTION OF THE DISCLOSURE

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the disclosure as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

FIGS. 1-6 reference a multipurpose filament dispensing device 100, hereinafter "device" that serves the dual purpose of dispensing a filament 101, while also capping an opening 103 on a container 105 of topical ointment. Typical containers of topical ointment such as lip balm are universal in size and shape and thus filament dispensing device 100 can be used interchangeably with the variety of manufactured lip balm containers or can be used as a standalone item. The device 100 can either function as a standalone dispenser for storing and dispensing the filament, or serve as a cap for the container while simultaneously storing and dispensing the filament. In one embodiment, the device 100 dispenses the filament from a raised outlet 122 and extends the filament to a depressed cutting member 144 to facilitate grasping, manipulating, and cutting of the filament. The device 100 may also mate with an opening of the container to form a detachable cap thereto.

In some embodiments, the filament can be rotatably extracted from an internal spool 138 in the device 100. The filament is wound around the spool 138 for storage, and unwound for dispensing. After extracting a desired unit length of the filament, the filament is extended at a slope from a raiser outlet to a depressed cutting member 144, and finally cut to a desired unit length. The slope creates a space beneath the filament that facilitates handling of the filament. The filament may include, without limitation, dental floss, a string, and an interdental cleaning member.

In some embodiments, the device 100 forms a detachable cap over the container. The container may hold a topical composition. The topical composition may include, without limitation, a lip balm, a lip salve, or other lip application. The topical composition dispenses from an opening in the container. In one embodiment, the device 100 detaches from the opening to enable access to the topical composition. In yet another embodiment, the filament and/or the topical composition can be compacted into the attached container, such that space is optimized to enhance portability. In one embodiment, the device 100 can be small enough to fit in a purse or pocket.

Figure 1:
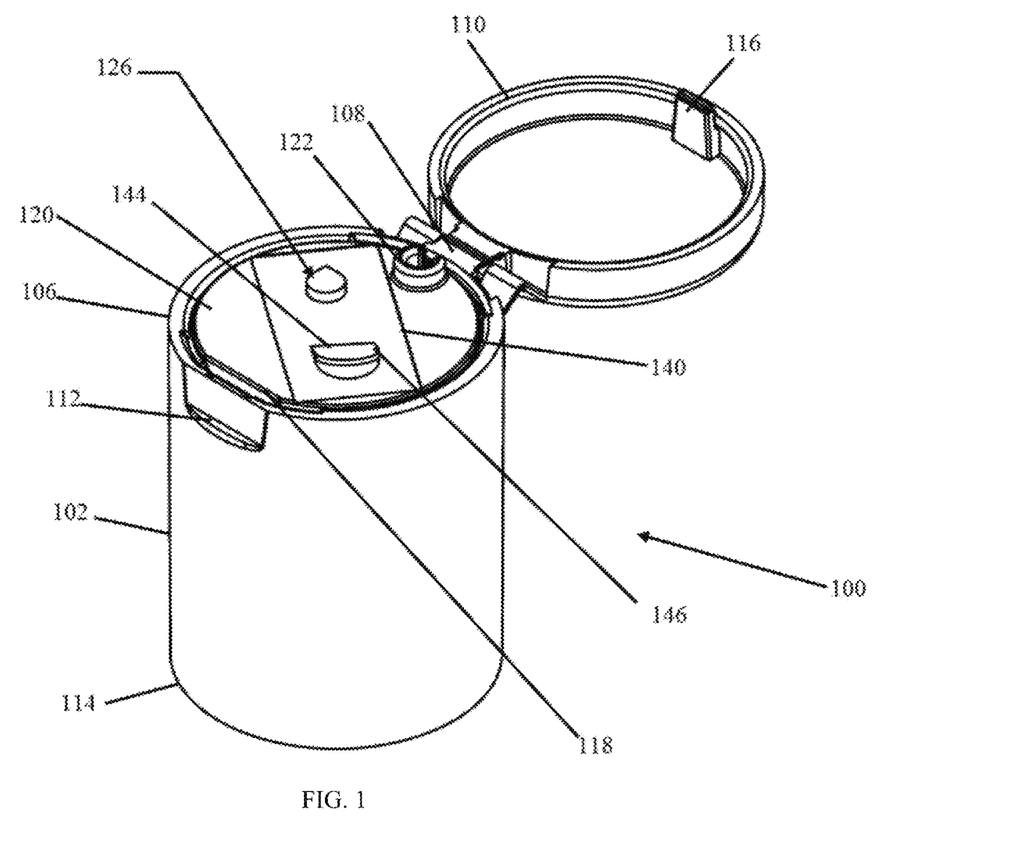
FIG. 1 illustrates a detailed perspective view of an exemplary multipurpose filament dispensing device, in accordance with an embodiment of the present disclosure.

As referenced in FIG. 1, the device 100 dispenses a filament from a raised outlet 122, and extends the filament to a depressed cutting member 144 to enable facilitated grasping and cutting of the filament. The device 100 also caps an opening on a container of a topical composition. The device 100 comprises an outer housing 102 that substantially encases an inner housing 118. Both housings 102, 118 are arranged to work together to efficiently dispense the filament efficiently, and securely cap the opening in an attached container.

Figure 2:
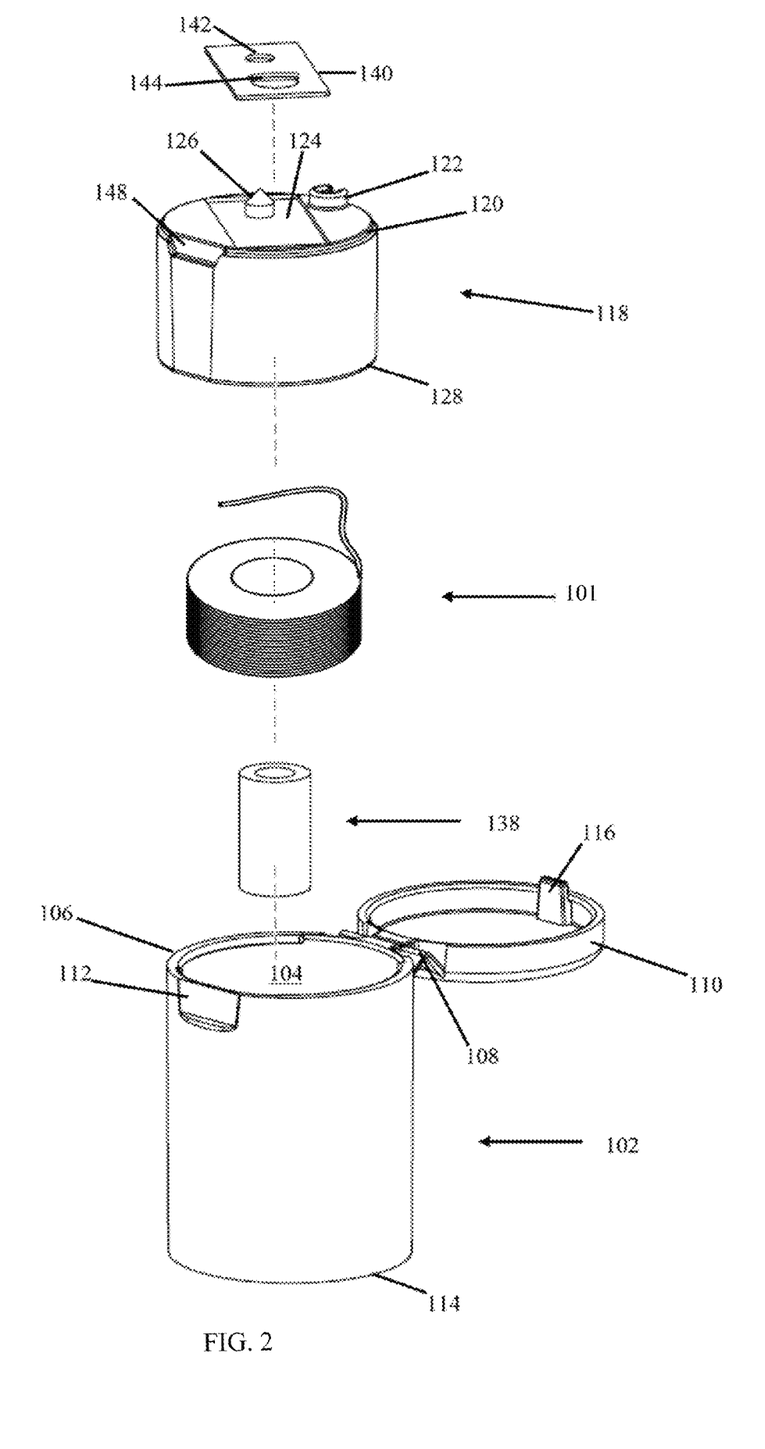
FIG. 2 illustrates a exploded view of the multipurpose filament dispensing device, in accordance with an embodiment of the present disclosure.

FIG. 2 illustrates an exploded view of the device 100, illustrating how the inner housing 118 is sized to snap/lock inside the outer housing 102. Inner housing 118 encases a spool 138 that carries a roll of filament. The inner housing 118 also facilitates grasping, manipulating, and cutting of the filament 101. The inner housing 118 is defined by a dispensing end 120, a circular wall end 128, and an interior chamber 130. The inner housing 118 is disposed to position inside the cavity 104 of the outer housing 102, wherein the dispensing end 120 and the outlet end 106 are in a spaced-apart parallel arrangement. In one embodiment, the inner housing 118 snaps/locks inside the cavity 104 of the outer housing 102. Suitable materials for the inner housing 118 may include, without limitation, a rigid polymer, polyurethane, polyvinylchloride, rubber, metal, fiberglass, and wood.

Device 100 includes a panel 140 that includes a cutting member 144 that has a sharp edge 146 that is capable of cutting the filament to a desired unit length during use. The panel 140 is disposed to engage the depression 124 of the dispensing end 120. Specifically, the panel 140 is substantially shaped to rest flush inside the depression 124 of the dispensing end 120. The panel 140 is defined by a panel opening 142 and a cutting member 144. The panel opening 142 is configured to interlock with the protrusion 126 of the dispensing end 120.

In one embodiment, heat staking is used to fasten the panel 140 to the dispensing end 120. In this process, the panel opening 142 enables passage of the protrusion 126. The polymers are then melted to form a unitary piece that interlocks the panel opening 142 and the depression 124. This may create a mushrooming effect. However, in other embodiments, the panel opening 142 may interlock with the protrusion 126 through a frictional fit, a ridged mating, a magnetic lock, or an adhesive. In any case, the panel 140 positions securely inside the depression 124 of the dispensing end 120. The panel 140 is fabricated from a thin sheet of metal or other sturdy material capable of positioning a cutting member 144.

Cutting member 144 serves to cut the filament at a desired unit length. The cutting member 144 is disposed at one end of the panel 140. The cutting member 144 has a generally sharp edge 146, such as a blade, a razor or a jagged section of metal. The sharp edge 146 of the cutting member 144 is configured to help guide the filament to enable separation of a unit length of dispensed filament from a section of filament wound on the spool 138. The sharp edge 146 may be formed in a semi-circular shape to allow for cutting from either side of the blade; though the radius may be increased or decreased to affect the cutting capacity. The cutting member 144 extends from the panel 140 at a slope. The slope creates a space between the cutting member 144 and panel 140 that that facilitates cutting the filament.

Additionally, since the panel 140, and thereby the cutting member 144, are disposed within the depression 124, the raised outlet 122 is generally at a higher elevation (FIG. 1). Thus, as the filament dispenses from the raised outlet 122, the filament extends at a downward angle towards the cutting member 144 for cutting. This sloped extension of filament from the raised outlet 122 to the cutting member 144 forms a space beneath the filament that facilitates manipulation and grasping of the filament. In essence, the difference in elevation between the raised outlet 122 and the cutting member 144 is configured to enable facilitated cutting of the filament.

Figure 3:
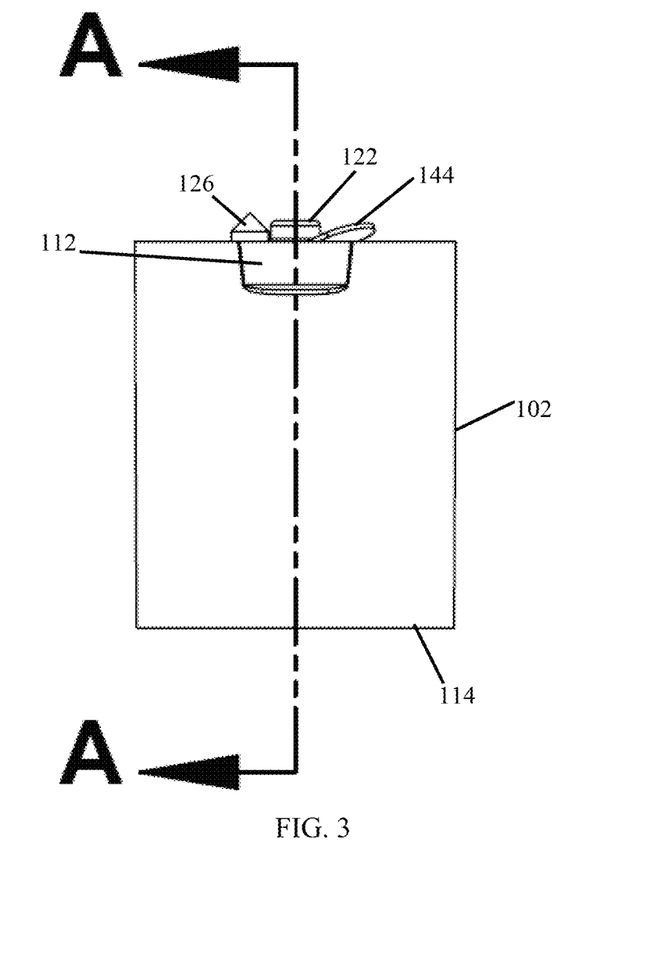
FIG. 3 illustrates an elevated side view of the multipurpose filament dispensing device, in accordance with an embodiment of the present disclosure.
Figure 4:
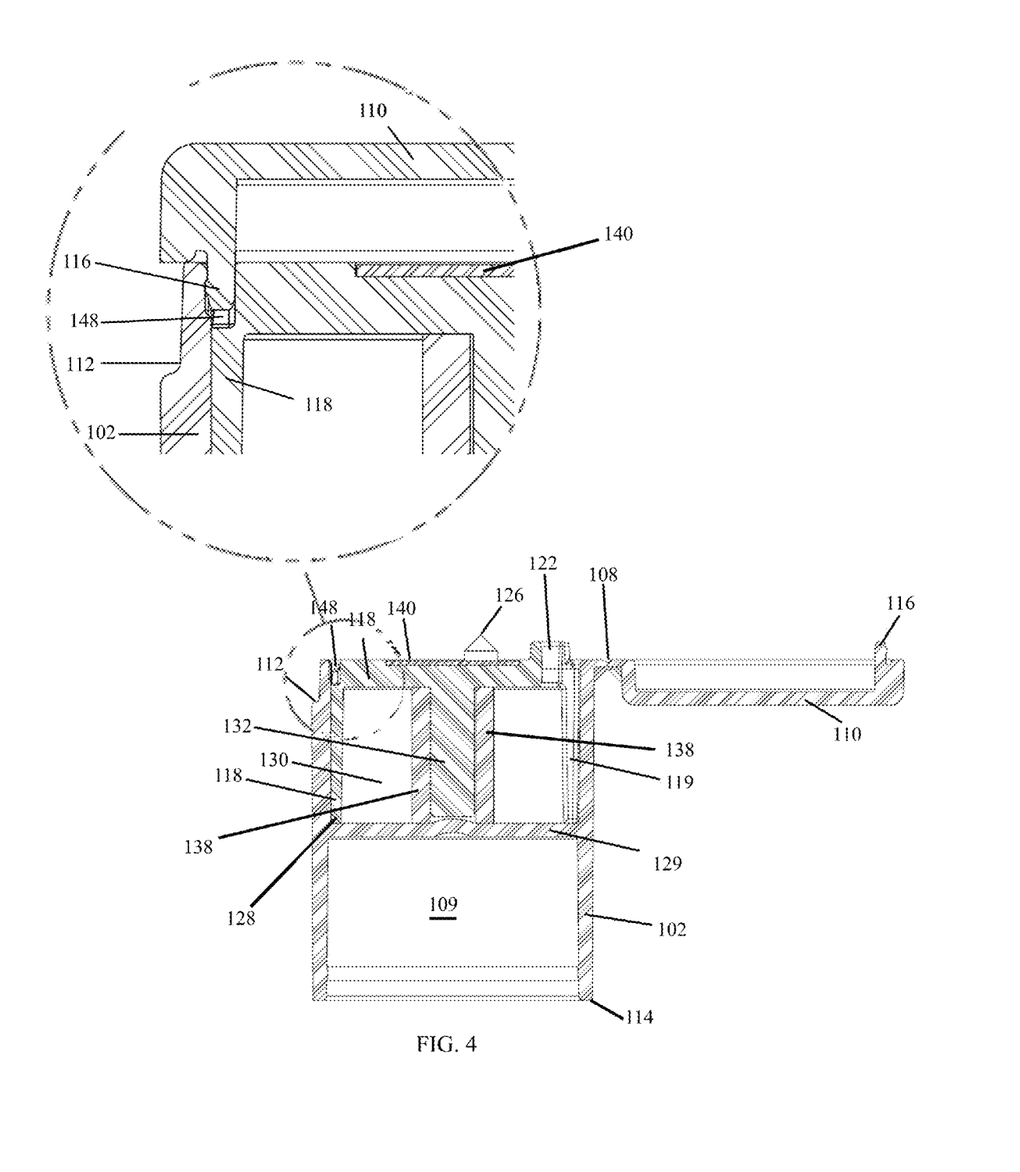
FIG. 4 illustrates a cross sectioned perspective side view of the multipurpose filament dispensing device generally taken along section A-A of FIG. 3 with a close-up of an exemplary lid that is latched to an exemplary dispensing end of an outer housing, in accordance with an embodiment of the present disclosure.

FIG. 3 illustrates an elevated side view of the multipurpose filament dispensing device, in accordance with an embodiment of the present disclosure. FIG. 4 illustrates a cross sectioned perspective side view of the multipurpose filament dispensing device generally taken along section A-A of FIG. 3 with a close-up of an exemplary lid that is latched to an exemplary dispensing end of an outer housing, in accordance with an embodiment of the present disclosure. Outer housing 102 engages the opening in the container and forms a protective casing for the inner housing 118. The outer housing 102 is defined by an upper cavity 104, a lower cavity 109, an outlet end 106, a mounting end 114, and a lid 110. The outer housing upper cavity and lower cavity is separated by wall 129. In one embodiment, the outer housing 102 is generally circular and has a diameter substantially the same as the container that is being capped. The lid 110 is configured to regulate access to the cavity 104. In one embodiment, a hinge 108 forms a junction between the lid 110 and the outlet end 106 of the outer housing 102 to enable pivotal movement of the lid 110 between an open position and a closed position. The lid 110 has a latching member 116. The latching member 116 frictionally engages indentation 148 of the lid 110 proximate to the perimeter ridge 112 for securing the lid 110 in the closed position and for enabling latching member to engage a bottom edge of the lid 110. When the lid is in a closed position and locked, the perimeter ridge 112 allows for easy engagement of the lid. The slight indentation allows the user to gain purchase with a fingernail or an edge of the finger to grip and open the lid. The outside surface of the housing is generally smooth so it is necessary to have an indentation to allow the user a place to engage and easily flip the lid open.

Figure 5A:
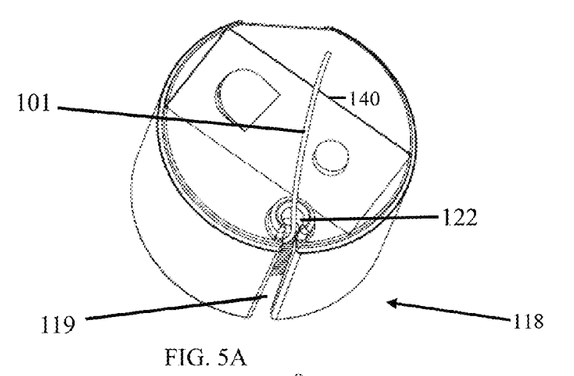
FIG. 5A illustrates a perspective top view of the inner housing of the multipurpose filament dispensing device, in accordance with an embodiment of the present disclosure.

FIG. 5A illustrates a perspective top view of the inner housing of the multipurpose filament dispensing device, in accordance with an embodiment of the present disclosure, the dispensing end 120 of the inner housing 118 is disposed distally from the container. The dispensing end 120 comprises a raised outlet 122, a depression 124, and a protrusion 126. The raised outlet 122 is in communication with the interior chamber 130 of the inner housing 118.

In one embodiment, the depression 124 may have a generally rectangular shape and occupy one side of the dispensing end 120. The protrusion 126 may include a generally conical shape. In yet another embodiment, the inner housing 118 may have an indentation 148 on the dispensing end 120. The indentation 148 frictionally engages the latching member of the lid 110 while the lid is in the closed position to form a more securely closed cap.

A filament guide 119 is used to guide one end of the filament from the spool 138 to the raised outlet 122. The filament guide may include a channel that is sized and dimensioned to receive and guide a free end of the filament from the spool 138 to the raised outlet 122. The filament guide 119 is a channel that works in conjunction with raised outlet 122 which is a generally C-shaped opening. The filament is pulled along the channel through the gap of the C-shaped opening to the exterior of the housing. If raised outlet 122 was configured with a "closed" 0-shaped opening it would be difficult to thread the filament through the opening. Once the inner housing is placed within the outer housing the gap of filament guide 119 is effectively closed by the exterior wall of the outer housing. The filament used in this device may include, without limitation, dental floss, string, and dental related flossing members.

Figure 5B:
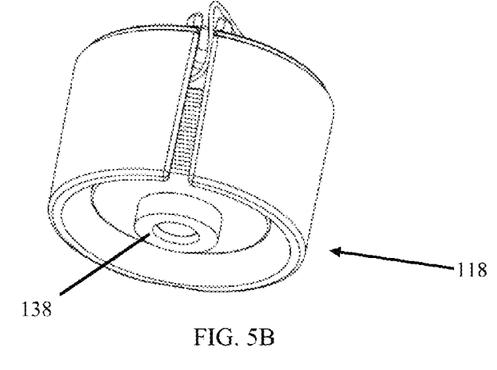
FIG. 5B illustrates an prospective bottom view of the inner housing of the multipurpose filament dispensing device, in accordance with an embodiment of the present disclosure.

FIG. 5B illustrates an prospective bottom view of the inner housing of the multipurpose filament dispensing device, in accordance with an embodiment of the present disclosure Spool post 132 is disposed in the interior chamber 130 of the inner housing 118. The spool post 132 is configured to rotatably hold a spool 138 that carries the filament 101. The spool post 132 extends along the length of the inner housing the spool housing. The spool 138 rotatably mounts to the spool post and is configured to carry filament. The filament winds around the spool 138 for storage, and may be unwound to dispense the filament from the elevated outlet.

Figure 5C:
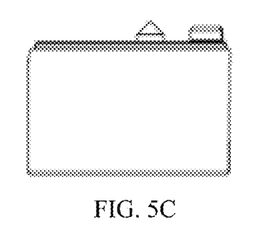
FIG. 5C illustrates a side view of the inner housing of the multipurpose filament dispensing device, in accordance with an embodiment of the present disclosure.
Figure 5D:
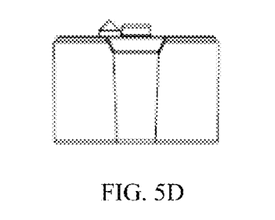
FIG. 5D illustrates a side view of the inner housing multipurpose of the filament dispensing device, in accordance with an embodiment of the present disclosure.

FIG. 5C illustrates a side view of the inner housing of the multipurpose filament dispensing device, in accordance with an embodiment of the present disclosure. FIG. 5D illustrates a side view of the inner housing of the multipurpose filament dispensing device, in accordance with an embodiment of the present disclosure.

Figure 5E:
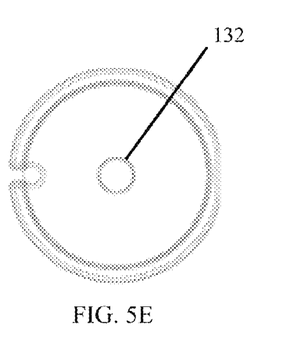
FIG. 5E illustrates a bottom view of the inner housing of the multipurpose filament dispensing device, in accordance with an embodiment of the present disclosure.

FIG. 5E illustrates a bottom view of the multipurpose filament dispensing device, in accordance with an embodiment of the present disclosure. Raised outlet 122 has a generally C-shaped circular opening that enables passage of the filament from the interior chamber 130. However, in other embodiments, the raised outlet 122 may take other shapes, including, without limitation, cubicle, rectangular, and triangular. The depression 124 and the protrusion 126 enable secure positioning of components for accessing, manipulating, and cutting the filament, as described below. Spool post 132 is cylindrical post operatively arranged to rotatably accommodate a spool of filament. The spool post is fixed to the center of under-side of dispensing end of the inner housing. The spool post extends the length of the inner housing wall and is of sufficient length to hover above wall 129 of the outer housing when the inner housing is inserted into the outer housing.

In one embodiment, the depression 124 may have a generally rectangular shape and occupy one side of the dispensing end 120. The protrusion 126 may include a generally conical shape. In yet another embodiment, the inner housing 118 may have an indentation 148 on the dispensing end 120. The indentation 148 frictionally engages the latching member of the lid 110 while the lid is in the closed position to form a more securely closed cap.

A filament guide may be used to guide one end of the filament from the spool 138 to the raised outlet 122. The filament guide may include a channel that is sized and dimensioned to receive and guide a free end of the filament from the spool 138 to the raised outlet 122. The filament may include, without limitation, dental floss, string, and dental related flossing members.

Figure 6A:
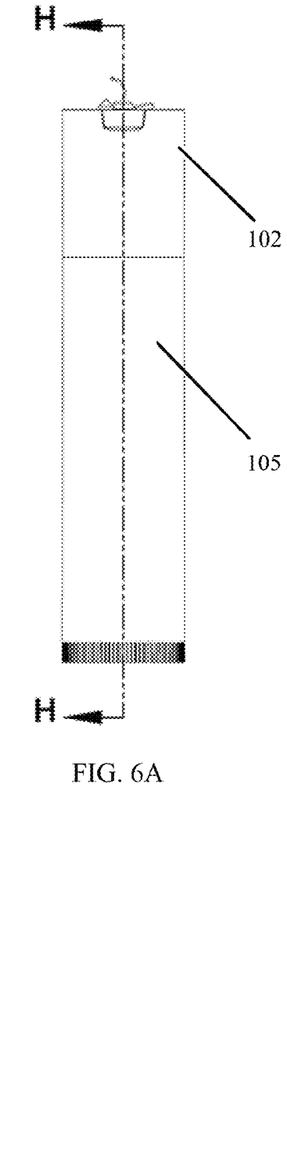
FIG. 6A illustrates a side view of the multipurpose filament dispensing device connected to an exemplary container of topical ointment, in accordance with an embodiment of the present disclosure.
Figure 6B:
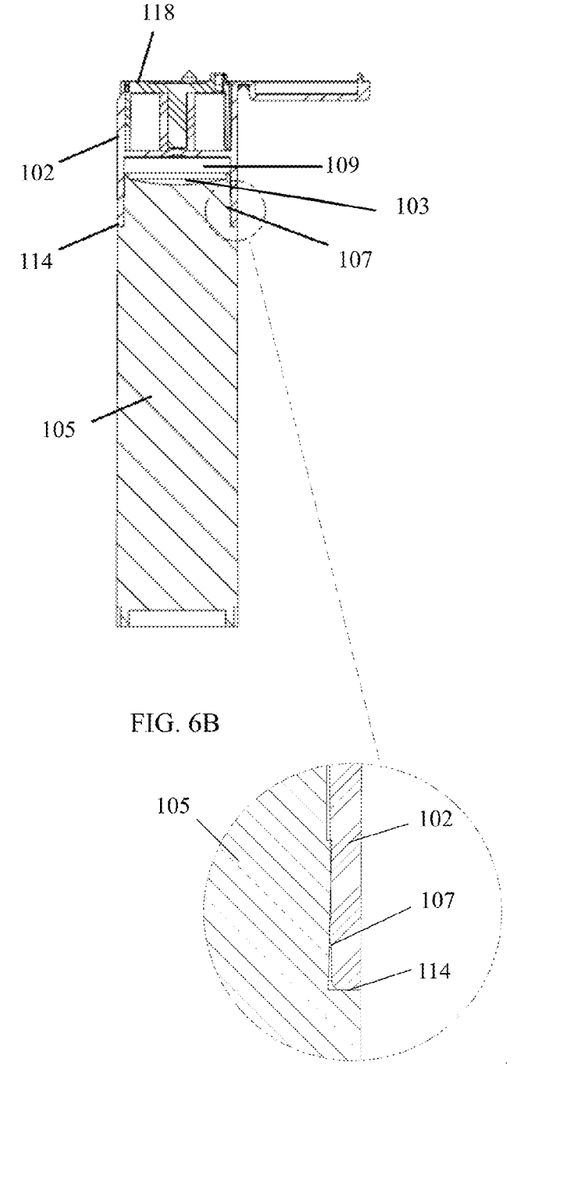
FIG. 6B illustrates a sectioned side view of the multipurpose filament dispensing device, the section generally taken along section H-H of FIG. 6A, detailing an interior chamber of the inner housing inside the outer housing connected to an exemplary container of topical ointment, in accordance with an embodiment of the present disclosure.

FIG. 6A illustrates a side view of the multipurpose filament dispensing device connected to an exemplary container of topical ointment, in accordance with an embodiment of the present disclosure. FIG. 6B illustrates a sectioned side view of the multipurpose filament dispensing device, the section generally taken along section H-H of FIG. 6A, detailing an interior chamber of the inner housing inside the outer housing connected to an exemplary container of topical ointment, in accordance with an embodiment of the present disclosure. The mounting end 114 of the outer housing 102 is oppositely positioned from the outlet end 106, and configured to enable engagement with the opening of the container. The mounting end 114 can mate with the opening through various mechanisms, including, without limitation, threaded engagement, frictional fit, interlocking ridges, magnets, and screws. In this manner, the outer housing 102 forms a cap to the opening. Suitable materials for the outer housing 102 may include, without limitation, a rigid polymer, polyurethane, polyvinylchloride, rubber, metal, fiberglass, and wood. In another embodiment, the outer housing 102 displays indicia, graphics, text, and logos to help identify the topical composition and the filament.

Cavity 109 of outer housing 102 is cylindrical he shaped and configured to fit over an opening 103 of container 105 that is in this example a container of topical composition such as lip balm or the like. The cylindrical cavity at the top of lip balm container will typically contain a movable cylindrical stick of lip balm. A fastening means 107 positions proximate mounting end 114 and serves to fasten the device 100 to the outside of the typical cylindrical lip balm container. The fastening means may include, without limitation, a lip that engages a channel, a threaded mating surface, and a magnet and the like. It should be readily apparent that the outer housing 102, positioned atop the container, helps inhibit contamination of the topical composition by external elements and also protects against undesirable drying of the topical composition. In this manner, the device 100 optimizes space by combining the container capping function and the filament dispensing functions.

Figure 7:
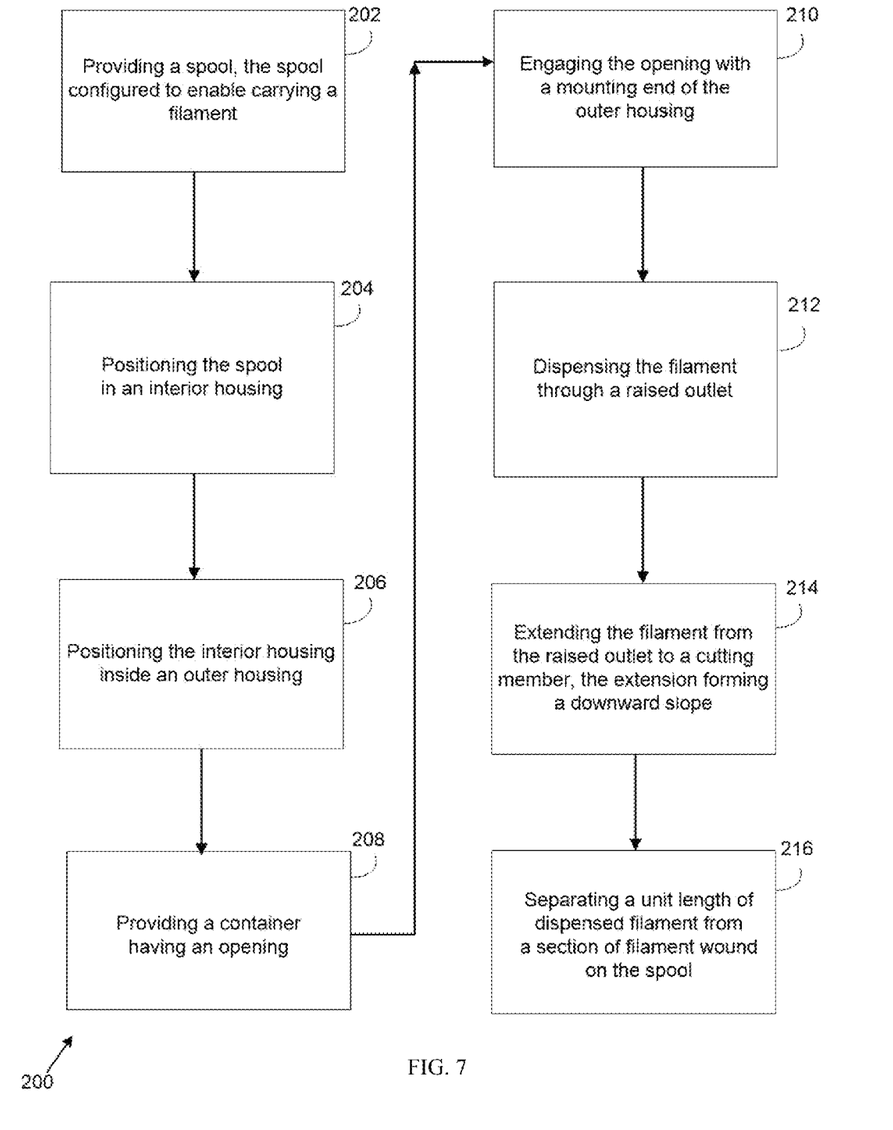
FIG. 7 illustrates a flowchart diagram of an exemplary method for dispensing a filament and capping an opening with a multipurpose filament dispensing device, in accordance with an embodiment of the present disclosure.

FIG. 7 illustrates a flowchart diagram of an exemplary method 200 for dispensing a filament and capping an opening with a multipurpose filament dispensing device 100. The method 200 utilizes the device 100 for the dual purpose of dispensing a filament, while also capping an opening. In one embodiment, the method 200 enables the device 100 to dispense the filament from a raised outlet 122 and extend the filament to a depressed cutting member 144 to facilitate grasping, manipulating, and cutting of the filament. The method 200 also allows the device 100 to mate with an opening of a container of topical composition.

The method 200 may include an initial Step 202 of providing a spool 138, the spool 138 configured to enable carrying a filament. The filament may include dental floss. However, in other embodiments, any filament in a variety of industries and arts may be used. The method 200 may further comprise a Step 204 of positioning the spool 138 in an inner housing 118. A spool post 132 is disposed in the interior chamber 130 of the inner housing 118. The spool 138 is configured to carry a filament. The filament winds around the spool 138 for storage, and may be unwound to dispense the filament from the elevated outlet. A filament guide serves to guide one end of the filament from the spool 138 to the raised outlet 122. The filament guide may include a channel that is sized and dimensioned to receive and guide the filament from the spool 138 to the raised outlet 122. The filament may include, without limitation, dental floss.

A Step 206 includes positioning the inner housing 118 inside an outer housing 102. The inner housing 118 is disposed to position inside the cavity 104 of the outer housing 102, wherein the dispensing end 120 and the outlet end 106 are in a spaced-apart parallel arrangement. In some embodiments of the method 200, a Step 208 comprises providing a container having an opening. The device 100 forms a detachable cap over the container. The container may hold a topical composition. The topical composition may include, without limitation, a lip balm, a lip salve, or other lip application. The topical composition dispenses from an opening in the container. The device 100 detaches from the opening to enable access to the topical composition.

A Step 210 includes engaging the opening with a mounting end 114 of the outer housing 102. The outer housing 102 of the device 100 may be configured to fit over an opening of a container that contains a topical composition. A fastening member positions on the lower edge of the mounting end 114 and serves to secure the device 100 to the container. In some embodiments, a Step 212 may include dispensing the filament through a raised outlet 122. The dispensing end 120 of the inner housing 118 is comprised of a raised outlet 122, a depression 124, and a protrusion 126. The raised outlet 122 is in communication with the interior chamber 130 of the inner housing 118. In one embodiment, the raised outlet 122 may include a generally circular opening that enables passage of the filament from the interior chamber 130.

A Step 214 comprises extending the filament from the raised outlet 122 to a cutting member 144, the extension forming a downward slope. Since the panel 140, and thereby the cutting member 144, are disposed in the depression 124, the raised outlet 122 is generally at a higher elevation. Thus, as the filament dispenses from the raised outlet 122, the filament extends at a downward angle towards the cutting member 144 for cutting. This sloped extension of filament from the raised outlet 122 to the cutting member 144 forms a space beneath the filament that facilitates manipulation and grasping of the filament. A final Step 216 includes separating a unit length of dispensed filament from a section of filament wound on the spool 138. The cutting member 144 serves to cut the filament at a desired length. The cutting member 144 is disposed at one end of the panel 140.

The cutting member 144 has a generally sharp edge 146, such as a razor or a jagged section of metal. The sharp edge 146 of the cutting member 144 is configured to enable separation of a unit length of dispensed filament from a section of filament wound on the spool 138. Though, specifically, the small space where the panel 140 and cutting member 144 meet is where the filament is cut. Therefore the filament can be cut on either side of the slope.

These and other advantages of the disclosure will be further understood and appreciated by those skilled in the art by reference to the following written specification, claims and appended drawings.

Since many modifications, variations, and changes in detail can be made to the described preferred embodiments of the disclosure, it is intended that all matters in the foregoing description and shown in the accompanying drawings be interpreted as illustrative and not in a limiting sense. Thus, the scope of the disclosure should be determined by the appended claims and their legal equivalence.

What I claim is:

1. A combination container and filament dispensing device for dispensing a filament and capping an-opening, the device comprising:
    an outer housing, the outer housing defined by an upper cavity and a lower cavity separated by an internal wall, an outlet end, a mounting end, and a lid,
    the lid configured to regulate access to the upper cavity, the mounting end of the lower cavity removably caps an opening of the container;
    an inner housing, the inner housing defined by a dispensing end, a cap end, and an interior chamber,
    the inner housing disposed to position inside the upper cavity of the outer housing, wherein the dispensing end and the outlet end are in a spaced-apart parallel arrangement,
    the dispensing end having a raised outlet, a depression, and a protrusion,
    the raised outlet arranged in communication with the interior chamber of the inner housing;
    a spool post, the spool post disposed in the interior chamber of the inner housing;
    a spool, the spool disposed to rotatably mount the spool post, the spool configured to enable carrying a filament; and
    a panel, the panel disposed to engage the depression of the dispensing end, the panel defined by a panel opening and a cutting member,
    the panel opening configured to interlock with the protrusion of the dispensing end,
    the cutting member having a generally sharp edge, the cutting member disposed at a generally lower elevation than the raised outlet,
    wherein the difference in elevation between the raised outlet and the cutting member is configured to enable facilitated access to the filament,
    wherein the sharp edge of the cutting member is configured to enable separation of a unit length of dispensed filament from a section of filament wound on the spool.

2. The device of claim 1, wherein the filament is a dental floss.

3. The device of claim 1, wherein the container contains a topical composition.

4. The device of claim 3, wherein the topical composition is a lip balm.

5. The device of claim 1, wherein the container has a generally cylindrical shape with a diameter that substantially matches the diameter of the mounting end of the outer housing.

6. The device of claim 1, wherein the outer housing comprises a hinge, the hinge configured to enable the lid to pivotally move between an open position and a closed position relative to the outlet end.

7. The device of claim 6, wherein the outlet end has a perimeter ridge.

8. The device of claim 7, wherein the lid has a latching member.

9. The device of claim 8, wherein the perimeter ridge is configured to leave a gap between the exterior of the housing and the edge of the lid to enable a finger to lift the lid.

10. The device of claim 1, wherein the inner housing exterior wall has a longitudinal gap as a filament guide, the filament guide configured to guide the filament from the spool to the raised outlet.

11. The device of claim 1, wherein the spool post comprises a cylindrical post, the post configured to rotatably hold the spool in the exterior of the inner housing.

12. The device of claim 1, wherein the panel opening and the protrusion from the dispensing end are interlocked through a beat staking process.

13. The device of claim 1, wherein the panel is substantially rectangular.

14. The device of claim 1, wherein the panel is a metal composition.

15. The device of claim 1, wherein the cutting member extends form the panel at an upward angle.

16. The device of claim 1, wherein the cutting member forms a substantially semicircular shape having a sharp edge.

17. A combination container and filament dispensing device for dispensing a dental floss and capping an opening, the device comprising:

an outer housing, the outer housing defined by an upper cavity and a lower cavity separated by an interior wall, an outlet end, a mounting end, and a lid, the lid configured to regulate access to the upper cavity by pivotally moving between an open position and a closed position on a binge, the mounting end removably caps an opening of the container containing a topical ointment;

an inner housing, the inner housing defined by a dispensing end, a cap end, and an interior chamber, the inner housing disposed to position inside the upper cavity of the outer housing, wherein the dispensing end and the outlet end are in a spaced-apart parallel arrangement, the dispensing end having a raised outlet, a depression, and a protrusion, the raised outlet arranged in communication with the interior chamber of the inner housing;

a spool post, the spool post disposed in the interior chamber of the inner housing;

a spool, the spool disposed to rotatably mount the spool post, the spool configured to enable carrying a dental floss; and a panel, the panel disposed to engage the depression of the dispensing end through heat staking, the panel shaped substantially the same as the depression, the panel defined by a panel opening and a cutting member, the panel opening configured to interlock with the protrusion of the dispensing end through a heat staking process, the cutting member having a generally sharp edge and semicircular shape, the cutting member disposed at a generally lower elevation than the raised outlet, wherein the difference in elevation between the raised outlet and the cutting member is configured to enable facilitated access to the dental floss, wherein the sharp edge of the cutting member is configured to enable separation of a unit length of dispensed dental floss from a section of dental floss wound on the spool.

* * * * *